United States Patent
Burtscher et al.

[11] Patent Number: 5,431,714
[45] Date of Patent: Jul. 11, 1995

[54] PROCESS FOR INVESTIGATING PARTICLES SITUATED IN A GAS

[75] Inventors: Heinz K. Burtscher, Zürich; Daniel A. Matter, Dietikon; Ulrich Kogelschatz, Hausen, all of Switzerland

[73] Assignee: ABB Research Ltd., Zurich, Switzerland

[21] Appl. No.: 202,136

[22] Filed: Feb. 25, 1994

[30] Foreign Application Priority Data

Feb. 25, 1993 [DE] Germany ............ 43 05 704.7

[51] Int. Cl.⁶ ................................. B03C 3/016
[52] U.S. Cl. .............................. 95/57; 55/270; 73/28.02; 95/70; 96/16; 96/55; 250/382; 250/423 P; 422/24
[58] Field of Search ............... 95/57, 6, 70; 73/28.01, 73/28.02; 96/16; 55/279, 270, 274; 422/22, 24, 121; 250/424, 375, 379, 382, 423 P

[56] References Cited

U.S. PATENT DOCUMENTS

| | | | |
|---|---|---|---|
| 3,313,971 | 4/1967 | Nagy | 96/16 X |
| 4,377,749 | 3/1983 | Young | 250/423 P |
| 4,750,917 | 6/1988 | Fujii | 96/16 X |
| 4,837,440 | 6/1989 | Burtscher et al. | 250/379 |
| 5,185,015 | 2/1993 | Searle | 422/121 X |
| 5,220,284 | 6/1993 | Ruegg et al. | 250/382 X |
| 5,288,305 | 2/1994 | Gellert et al. | 95/57 |

FOREIGN PATENT DOCUMENTS 3515258 11/1986 Germany.
4113929 9/1992 Germany.
972387 11/1982 U.S.S.R..

OTHER PUBLICATIONS

Eliasson et al., "Neue UV-Strahler fur industrielle Anwendungen", Publication CH-E 3.30833.0 D, (Reprint From ABB Technik), Mar., 1991, pp. 3-10.
Zeitschrift fur Phsikalische Chemie Neue Folge, Bd. 159, Von W. Robers, et al., "Photo-und Thremoionisation von Aerosolen durch gepulstes Laserlicht", pp. 129-148, Jan. 24, 1989.

Primary Examiner—Richard L. Chiesa
Attorney, Agent, or Firm—Oblon, Spivak, McClelland, Maier & Neustadt

[57] ABSTRACT

In the process for investigating particles situated in a gas, a gas stream is guided past a miniaturized UV excimer radiator. In this case, the particles are ionized and subsequently filtered out, and the resultant photoelectrically induced current is measured. Since particles from different sources (petrol engine, diesel engine, cigarette smoke) exhibit a wavelength dependence which is characteristic of the source, by measurements at at least two wavelengths, which is readily possible when using UV excimer radiators with different gas fillings, pollutants can be detected according to the source.

10 Claims, 3 Drawing Sheets

A-A

B-B

PROCESS FOR INVESTIGATING PARTICLES SITUATED IN A GAS

BACKGROUND OF THE INVENTION

1. Field of the Invention

The invention relates to the field of environmental metrology. It concerns, in particular, a process for investigating particles situated in a gas, in which process the gas containing the particles is guided in the form of a gas stream past a UV light source, the particles are ionized by the UV radiation from the UV light source, the ionized particles are filtered out from the gas stream and the photoelectrically induced current which is generated is measured.

Such a process is disclosed, for example, in U.S. Pat. No. 4,837,440 or DE-A-41 13 929.

2. Discussion of Background

On account of the increasing burdening of the environment with pollutants which, for example, are emitted by oil-fired heating systems or car and commercial vehicle traffic into the air, simple and reliable methods and equipment for measuring and monitoring the air quality are becoming progressively more important.

In this case, particular significance is ascribed to the particles which are in suspension in the air and which can be utilized for measuring the air quality for the following reason: in the course of any combustion of fossil fuels, very small carbon particles ($\phi < 0.1$ $\mu$m) are generated. In the course of the cooling of the combustion gas, a condensate may form on the surface of these particles, which condensate includes, inter alia, so-called polyaromatic hydrocarbons (PAHs). The concentration of these PAHs is a good measure of the quality of the combustion; it also shows good correlation with other pollutants which are formed in the course of a poor combustion, especially with CO. By measuring the PAH concentration, it is thus also possible to make a statement concerning the quality of the air.

A known and acknowledged method for measuring the PAH concentration is based on the following principle: by irradiation with UV light (wavelength for example 185 nm), it is readily possible to ionize particles on the surface of which PAHs are situated. If the gas which contains such ionized particles is conducted, after separating off the electrons formed in the course of the ionization, through particle filter carrying (ion) filter which is mounted in an electrically insulated manner and is connected to a current amplifier, the current caused by the charged particles can be measured. This current is a measure of the concentration of particle-bound PAHs.

In the known measurement processes, low-pressure mercury vapor lamps are employed in the charging unit. The emission of these Hg lamps is principally in the region of 253.7 nm and is thus of too long a wavelength, in the case of many aerosols, to initiate photoemission. That part of the spectrum which can be used for these purposes is around 184.9 nm and is, in its intensity, more than 10 times smaller than the longer-wavelength part. Over and above this, UV radiation of 184.9 nm generates ozone. The measurement involves greater difficulties, since the inapplicable part of the spectrum must be filtered out. The UV intensity is, moreover, greatly dependent upon the temperature and the number of operating hours of the respective lamp. A UV power value which is to some extent stable is not obtained until approximately 30 to 60 minutes after switching on.

As the radiators employed hitherto are available only as external radiators, the charging efficiency is also relatively low.

SUMMARY OF THE INVENTION

Accordingly, one object of the invention is to provide a novel process for measuring the concentration of particle-bound polyaromatic hydrocarbons (PAHs), which process permits with simple means reliable as well as space-saving and energy-saving measurement of air quality and also of the quality of combustion processes.

In the case of a process of the initially mentioned type, this object is achieved in that a UV excimer radiator based on the principle of the silent electrical discharge is employed as UV light source.

The construction and mode of operation of such UV excimer radiators are known and are described, by way of example, in the company publication of the applicant "Novel UV radiators for industrial applications", publication CH-E 3.30833.0 D, a reprint from the company journal "ABB TECHNIK" March 1991, pp. 21–28, with respect to the construction and mode of operation. In addition to other parameters, the composition of the filling gas in particular determines the wavelength of the UV radiation generated. UV excimer radiators may accordingly be manufactured for various wavelengths and in this manner permit an optimal choice of the photon energy. Over and above this, such radiators are very stable, have a long service life, a high efficiency and a narrow-band emission.

For the reasons which were described in the introduction, by using UV excimer radiators it becomes economically possible for the first time to be able to investigate combustion aerosols qualitatively and quantitatively and to be able to draw conclusions as to the source of the aerosols from the measured values at the location of the sensor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
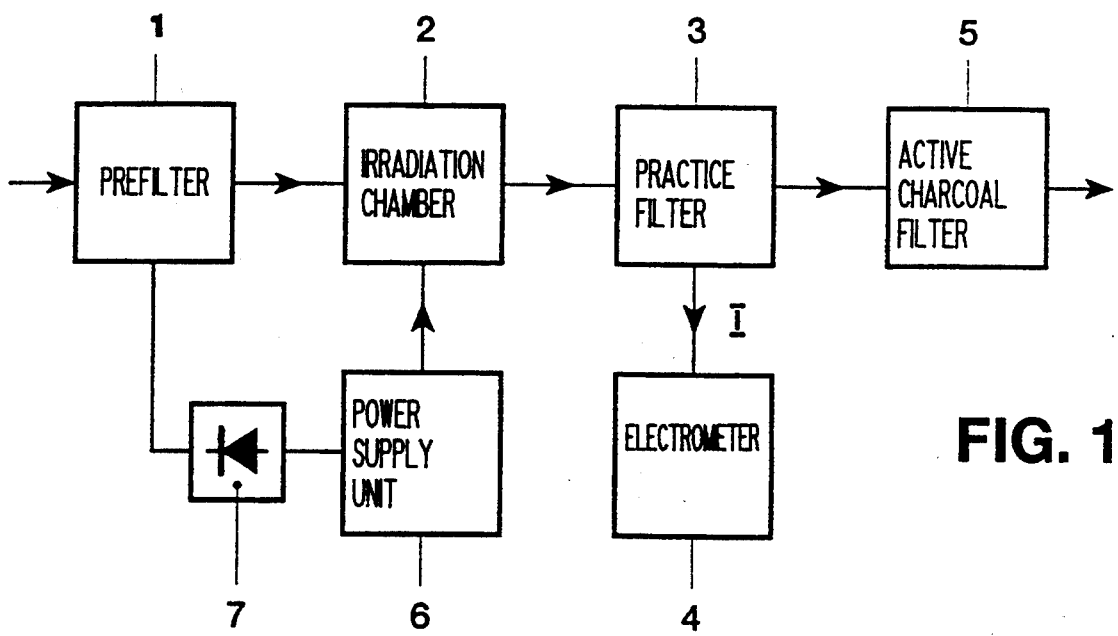
FIG. 1 shows a block diagram of a device for determining the air quality.

Referring now to the drawings, wherein like reference numerals designate identical or corresponding parts throughout the several views, in the block diagram according to FIG. 1 the aerosol-containing air to be investigated is conducted, after passing through a prefilter 1, through an irradiation chamber 2 and, in the latter, is exposed to UV radiation. At a sufficiently high photon energy, the aerosol particles emit electrons, and thus become photoelectrically charged. Downstream of the irradiation chamber 2, the very mobile negative ions, which were formed in the course of the emission of photoelectrons, are extracted by a weak electric field (approximately 10 V/cm). The far less mobile positively charged particles follow the gas stream and are extracted in a particle filter 3 mounted in an insulated manner. The current I which is caused by the charge flux into the particle filter 3 is measured by an electrometer 4. Downstream of the particle filter 3 there is optionally connected an active charcoal filter 5, in which ozone generated by the UV radiation is broken down.

Measuring arrangements of this type belong to the prior art and are also described, with respect to their constructional designs, for example in DE-A41 13 929 and in the numerous publications cited in this laid-open specification.

According to the invention, in the case of such a measuring arrangement there is provided a UV excimer radiator, which is based on the principle of the silent electrical discharges and the construction of which is described in detail hereinbelow.

UV excimer radiators are known per se (EP-A-0254 111). This type of radiator is based on the principle that it is also possible to generate excimer radiation in silent electrical discharges, a type of discharge which is employed on a large scale industrially in the production of ozone. In the filaments of current of this discharge, which exist only for a short period of time (<1 microsecond), noble gas atoms are excited by electron collision, which atoms further react to form excited molecular complexes (excimers). These excimers have a lifetime of only a few nanoseconds and, on being broken down, give off their energy in the form of UV radiation.

Since excimer radiators must be operated with alternating current at voltages of a few kV, it is recommended to obtain the supply voltage of the prefilter 1 from the power supply unit 6 of the UV excimer radiator, in that the high voltage with which the radiator is operated is rectified. This variant is symbolized in FIG. 1 by the broken connecting line between power supply unit 6 and prefilter 1 with interposed rectifier 7.

Figure 2:
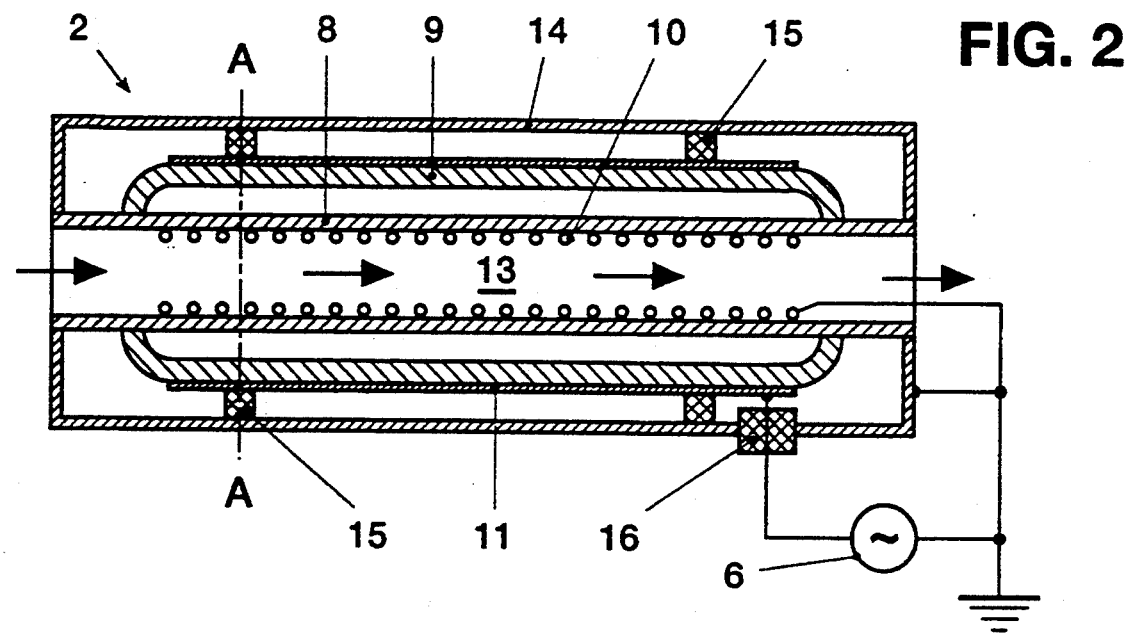
FIG. 2 shows a longitudinal section through a UV excimer radiator with internal radiant emission.
Figure 3:
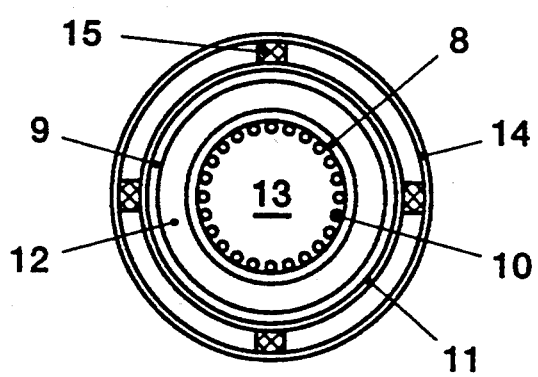
FIG. 3 shows a transverse section through the UV excimer radiator according to FIG. 2, along the line AA thereof.
Figure 4:
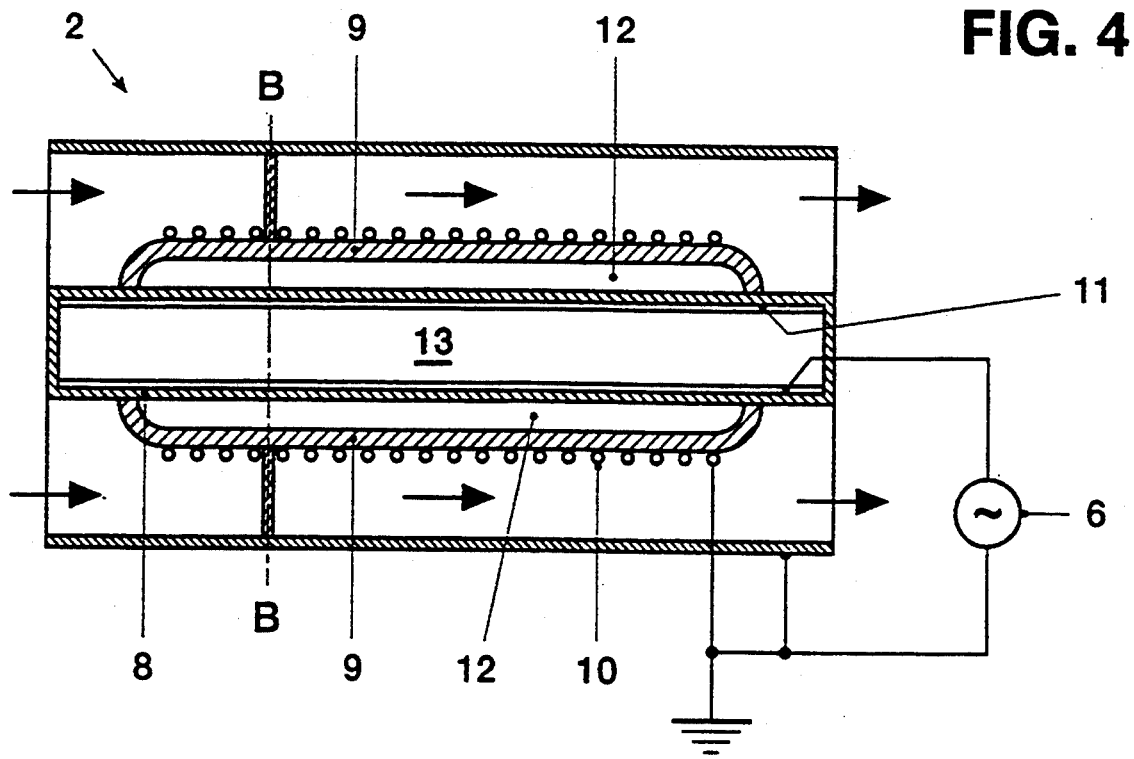
FIG. 4 shows a longitudinal section through a UV excimer radiator with external radiant emission.
Figure 5:
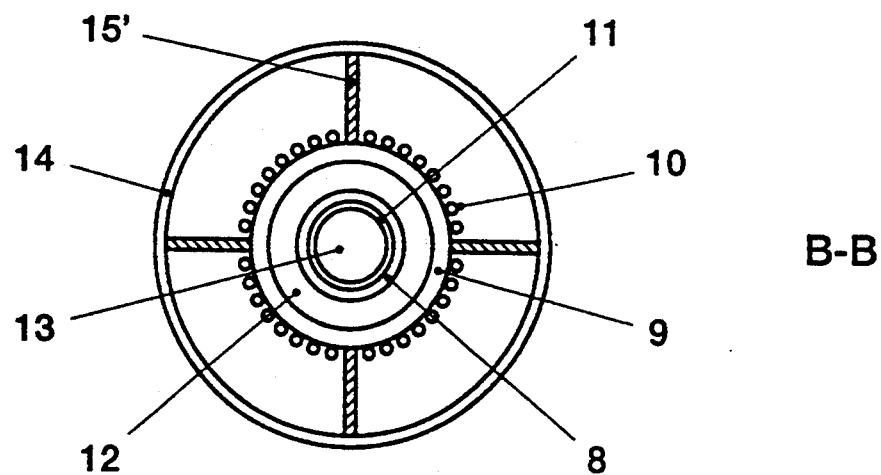
FIG. 5 shows a transverse section through the UV excimer radiator according to FIG. 4, along the line BB thereof.

Both internal radiators and also external radiators are employed as UV excimer radiators. FIGS. 2 and 3 show diagrammatically the construction of an internal radiator; FIGS. 4 and 5 show that of an external radiator.

According to FIGS. 2 and 3, an internal quartz tube 9 is coaxially disposed in an external quartz tube 8 having an external diameter of approximately 15 to 20 mm and a length of around 100 mm. An internal electrode in the form of a wire grid 10 rests on the internal surface of the internal quartz tube 9. Quartz tube 9 and wire grid 10 are transparent to the UV radiation generated.

An external electrode in the form of an aluminum layer 11 or aluminum foil extends over the entire external periphery of the external quartz tube 8. This aluminum layer 11 serves at the same time as reflector.

At both ends, the quartz tubes 8 and 9 are sealed by a respective cover or fused together. The space between the two tubes 8 and 9, the discharge space 12 with a typical gap width of 1 to 2 mm, is filled with a gas/gas mixture emitting radiation under discharge conditions.

The two electrodes 10 and 11 are connected to the two poles of the power supply unit 6; in this case, the internal electrode (wire grid 10) is at ground potential. The power supply unit 6 delivers a settable alternating voltage in the order of magnitude of a few hundred volts to 20,000 volts at frequencies within the range of industrial alternating current up to a few hundred kHz—depending upon the electrode geometry, pressure in the discharge space and composition of the filling gas.

The filling gas is, for example, mercury, noble gas, noble gas/metal vapor mixture, noble gas/halogen mixture, possibly with the use of an additional further noble gas, preferably Ar, He, Ne, as buffer gas. Depending upon the desired wavelength, in this case it is possible to use a gas/gas mixture according to the following table:

| Filling gas | Radiation |
| --- | --- |
| Helium | 60–100 nm |
| Neon | 80–90 nm |
| Argon | 107–165 nm |
| Argon + fluorine | 180–200 nm |
| Argon + chlorine | 165–190 nm |
| Argon + krypton + chlorine | 165–190, 200–240 nm |
| Xenon | 160–190 nm |
| Nitrogen | 337–415 nm |
| Krypton | 124, 140–160 nm |
| Krypton + fluorine | 240–255 nm |
| Krypton + chlorine | 200–240 nm |
| Mercury | 185, 254, 320–370 390–420 nm |
| Selenium | 196, 204, 206 nm |
| Deuterium | 150–250 nm |
| Xenon + fluorine | 340–360 nm, 400–550 nm |
| Xenon + chlorine | 300–320 nm |

In addition to the above, consideration may also be given to a whole series of further filling gases:
- a noble gas (Ar, He, Kr, Ne, Xe) or Hg with a gas or vapor selected from $F_2$, $I_2$, $Br_2$, $Cl_2$ or a compound which, in the discharge, splits off one or more F, I, Br or Cl atoms;
- a noble gas (Ar, He, Kr, Ne, Xe) or Hg with $O_2$ or a compound which, in the discharge, splits off one or more O atoms;
- a noble gas (Ar, He, Kr, Ne, Xe) with Hg.

When an alternating voltage is applied between the electrodes 3 and 4, a multiplicity of discharge channels (partial discharges) are formed in the discharge space 12. The relaxation of the atoms of the filling gas which are in this case excited leads to UV or VUV radiation.

In the silent electrical discharge which develops, the electron energy distribution can be set by thickness of the dielectrics and their properties as well as pressure and/or temperature in the discharge space, on an optimal basis.

In the case of the described internal radiator, the air to be investigated is conducted through the internal space 13 of the internal quartz tube 9. This air guidance has the advantage that as a result of the thermophoresis effect the internal quartz tube 8 is protected against contamination and thus against increasing UV absorption. A further advantage resides in that only relatively small quantities of ozone are generated in the environment of the radiator.

On the other hand, in the external radiator shown in longitudinal section and in transverse section respectively in FIGS. 4 and 5, the air to be investigated flows around the radiator. Accordingly, in this case the external electrode is designed as a wire grid 10, while the internal electrode is designed as an inserted aluminum sheet or as an aluminum coating 11 on the internal wall of the internal quartz tube 8 and also serves as reflector for the UV radiation generated in the discharge space 12. In contrast to the embodiment according to FIGS. 2 and 3, in this case the internal electrode 11 is at high-voltage potential and the external electrode (wire grid 10) is at ground potential.

In both embodiments, the UV excimer radiator is surrounded by a metallic housing 14 which is at ground potential. In the case of the external radiator, this housing wall can serve at the same time as reflector. In the case of the external radiator, the housing 14 is at the same electrical potential as the external electrode (wire grid 10); in the case of the internal radiator, it is at the potential of the internal electrode; in this case, the supporting of the external quartz tube 9 in relation to the housing 14 is insulated in high voltage resistant fashion by means of insulating spacers 15 and the high voltage supply to the external electrode 10 takes place via a high voltage lead-in 16.

It is advantageous in the case of both variants that electric stray fields at the lamp ends bring about a situation in which the very mobile negative small ions which are formed from the photoelectrons are drawn off, whilst the charged particles remain in the stream. As a result of this, an ion filter which is fitted in the former systems between irradiation chamber 2 and particle filter 3 is superfluous.

As has already been discussed in the introduction, particles from different sources (petrol engine, diesel engine, cigarette smoke) exhibit a dependence of the charge on the wavelength of the UV radiation acting on them, which dependence is characteristic of the source.

The following table shows the ratio of the photocurrent of a KrCl excimer radiator ($I_{PE222}$) of the wavelength 222 nm to that of an $Xe_2$ excimer radiator ($I_{PE172}$) of the wavelength 172 nm— the so-called charge coefficient $I_{PE222}/I_{PE172}$— for various combustion aerosols, namely garage aerosol ($A_{GAR}$), cigarette smoke ($A_{CIG}$) and diesel exhaust gas ($A_{DIES}$). The flow rate Q is 5 liters/min, and the electrical radiator power is 3 W. At the same time, the associated photothresholds and average particle diameters $D_{PART}$ are also indicated.

|  | $A_{GAR}$ | $A_{CIG}$ | DIES |
| --- | --- | --- | --- |
| $I_{PE222}/I_{PE172}$ | 0.8–1.0 | 0.07–0.08 | 0.16–0.21 |
| Photothreshold | 4.4 eV | 4.8–5.0 eV | 4.8 eV |
| $D_{PART}$ | 25 nm | 300–400 nm | 60 nm |

This compilation clearly reveals the dependence of the charge coefficient upon the composition of the aerosol. This dependence may now be utilized, according to the invention, in order to be able to distinguish aerosols from one another and finally to derive, from the value of the charge coefficient, useful data concerning the source of the aerosol.

Figure 6:
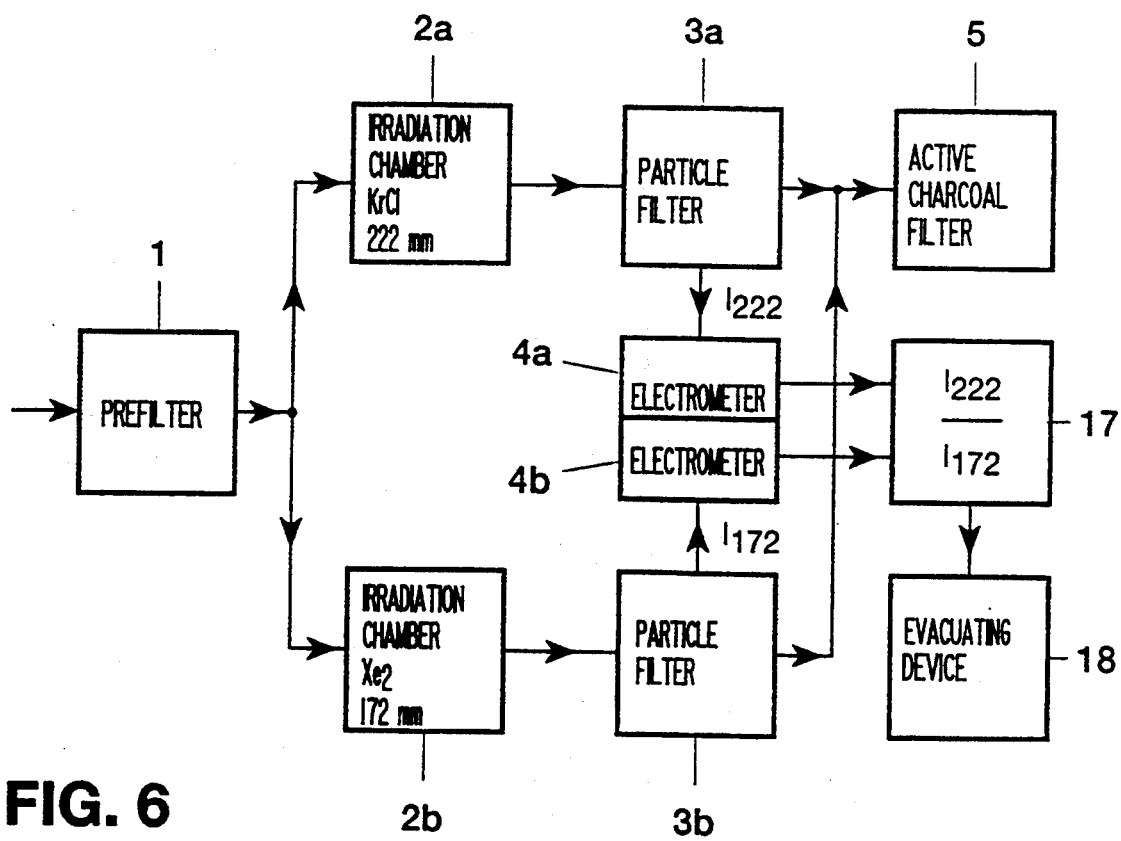
FIG. 6 shows a block diagram of a device for the qualitative and quantitative recording of the air quality with the use of two UV excimer radiators of differing wavelengths.

For this purpose, according to FIG. 6, the air which is to be investigated and which contains aerosols is caused to flow, after passing through the prefilter 1, through two parallel-connected irradiation chambers 2a and 2b and particle filters 3a and 3b. The irradiation chamber 2a is equipped with a krypton chloride excimer radiator (wavelength 222 nm), and the irradiation chamber 2b with an $Xe_2$ excimer radiator (wavelength 172 nm). Downstream of the parallelconnected particle filters 3a and 3b, the air streams recombine and pass into the active charcoal filter 5.

In the particle filters 3a and 3b, the current $I_{222}$ or $I_{172}$, which is caused by the charge flux into the filters 3a and 3b, is measured by a respective electrometer 4a or 4b. In a quotient former 17 connected downstream of the electrometers 4a and 4b, the charge coefficient $I_{PE222}/I_{PE172}$ is determined and fed in appropriate form to a downstream evaluating device 18. This evaluating device can for example be integrated into a house or security routing system or used generally for emission measurements.

Figure 7:
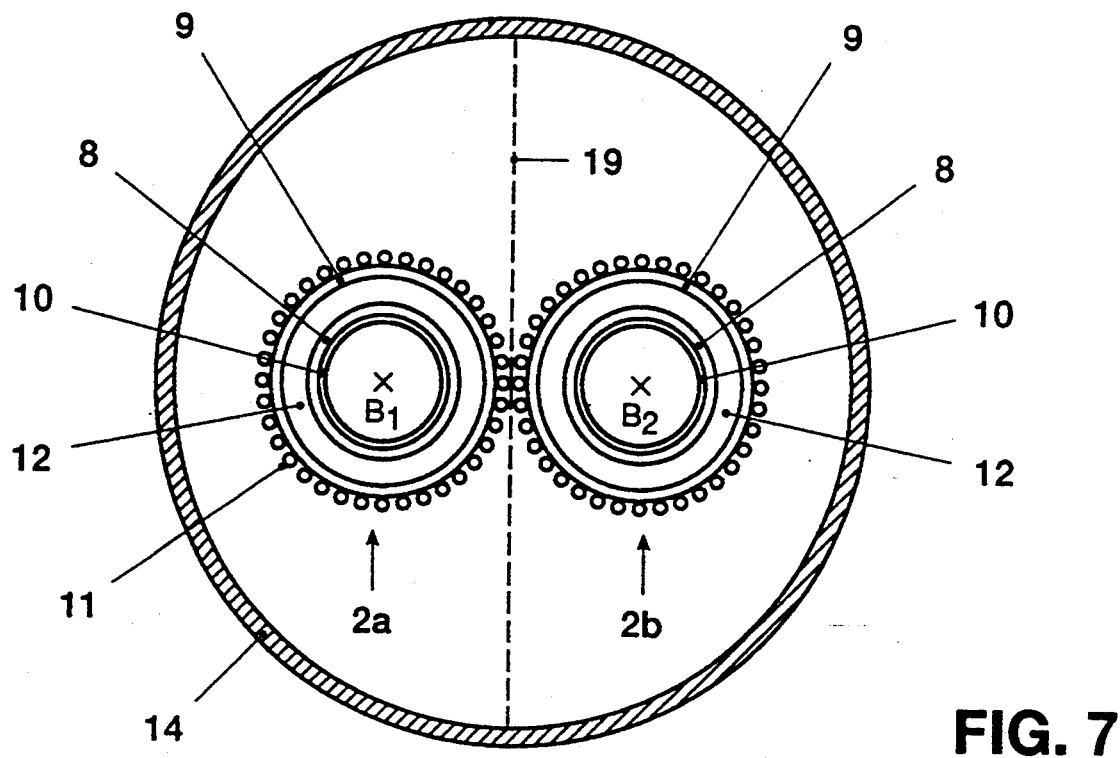
FIG. 7 shows a transverse section through an irradiation chamber with two UV excimer radiators, which generate UV radiation of differing wavelength.

On account of the compact type of construction of the UV excimer radiators and on account of their low power requirement, two or more UV excimer radiators of differing wavelengths can be incorporated into an irradiation chamber, as illustrated in FIG. 7. In the exemplary case, the two radiators 2a and 2b are designed as external radiators and exhibit the construction described in conjunction with FIG. 4 and FIG. 5. They are disposed in a housing 14 with elliptical cross section; in this case, their longitudinal axes coincide with the foci $B_1$ and $B_2$ of the ellipse. A separating wall 19 separates the two irradiation spaces into two portions having the same flow cross section.

The irradiation chamber according to FIG. 7 can now be operated in two different ways:

The more advantageous of the two modes of operation provides the operation of both radiators 2a and 2b in parallel and the feeding of the "irradiated" aerosols separately to the particle filters 3a and 3b, as shown in the block diagram according to FIG. 6. This has the advantage that the measurement result is available in real time.

The second mode of operation manages without a separating wall 19 and provides for the alternate switching on and off of the two UV excimer radiators 2a and 2b; in the case of such types of radiator, this is readily possible, since they deliver 95 to 98% UV emission, related to their final value, within a few seconds. Only one particle filter and accordingly also only one electrometer are then necessary. For the quotient formation, it is, however, necessary to place the first measured value into intermediate storage.

Of course, internal radiators according to FIGS. 2 and 3 can also be operated in the manner which has just been described.

The invention has been described hereinabove with reference to a cylindrical external or internal radiator. UV excimer radiators are—and this distinguishes them from conventional mercury radiators—capable of realization in many types of geometry, e.g. as flat-section radiators, as shown in the initially cited EP-A-0 254 111, FIG. 1 or FIG. 4. They can accordingly be adapted in ideal fashion to the measurement or monitoring function.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for investigating particles situated in a gas, comprising the steps of:
    providing two or more UV excimer radiators to generate UV radiation of differing wavelengths;
    guiding said gas past each of said UV excimer radiators so that each radiator ionizes a portion of said gas and produces respective ionized particles;
    filtering said respective ionized particles to produce respective photoelectrically induced currents;
    measuring said photoelectrically induced currents; and
    comparing the currents measured in said measuring step with one another.

2. The process according to claim 1, wherein:
    said providing step comprises providing an internal UV excimer radiator as said excimer radiator; and
    said guiding step comprises guiding said gas through said internal UV excimer radiator.

3. The process according to claim 1, wherein:
    said providing step comprises providing an external UV excimer radiator as said excimer radiator; and
    said guiding step comprises guiding said gas around said external UV excimer radiator.

4. The process according to claims 1, 2, or 3, wherein:
    said providing step comprises providing an electrostatic prefilter and a supply voltage common to said electrostatic prefilter and said UV excimer radiators; and
    said guiding step comprises guiding said gas through said electrostatic prefilter.

5. The process according to claims 1, 2, or 3, wherein said comparing step comprises:
    forming the ratio of the measured currents.

6. The process according to claim 4, wherein said comparing step comprises:
    forming the ratio of the measured currents.

7. The process according to claims 1, 2, or 3, further comprising:
    using a result of said comparing step as a regulating quantity in a routing system.

8. The process according to claim 4, further comprising:
    using a result of said comparing step as a regulating quantity in a routing system.

9. The process according to claim 5, further comprising:
    using the ratio of the measured currents as a regulating quantity for a routing system.

10. The process according to claim 6, further comprising:
    using the ratio of the measured currents as a regulating quantity for a routing system.

* * * * *